United States Patent [19]

Ando

[11] 4,398,183
[45] Aug. 9, 1983

[54] DETECTING METHOD AND APPARATUS FOR PERMANENT WAVE HAIRDRESSING

[75] Inventor: Akitoshi Ando, Itabashi, Japan

[73] Assignee: Kyoritsu Electrical Works, Ltd., Tokyo, Japan

[21] Appl. No.: 144,097

[22] Filed: Apr. 28, 1980

[51] Int. Cl.³ ............... G08B 23/00; G01N 31/22
[52] U.S. Cl. ..................... 340/500; 340/514; 340/573; 340/632; 116/207; 132/7; 422/56; 436/183
[58] Field of Search .......... 340/500, 501, 514, 573, 340/586, 588, 589, 632–634; 132/7; 116/206–208, DIG. 22, 44; 250/226; 422/56; 23/230 R, 232

[56] References Cited

U.S. PATENT DOCUMENTS

| | | | |
|---|---|---|---|
| 2,235,895 | 3/1941 | Maize | 132/7 |
| 3,139,328 | 6/1964 | Jacob | 422/56 |
| 3,980,437 | 9/1976 | Kishimoto et al. | 422/56 |
| 4,139,610 | 2/1979 | Miyazaki et al. | 132/7 |
| 4,158,704 | 6/1979 | Baer et al. | 132/7 |
| 4,174,202 | 11/1979 | Simpson | 422/56 |
| 4,228,810 | 10/1980 | Moore et al. | 132/7 |

Primary Examiner—Donnie L. Crosland
Attorney, Agent, or Firm—Sughrue, Mion, Zinn, Macpeak and Seas

[57] ABSTRACT

A method for detecting a condition of permanent waves during a permanent wave hairdressing, by using a chemical liquid which makes permanent waves and which produces a hydrogen sulfide gas at a predetermined temperature, and by exposing a lead acetate test paper to the hydrogen sulfide gas which changes colors to indicate the condition of the permanent wave. An apparatus having a light emitting diode detects the change in color of the test paper and activates a buzzer when a predetermined change of color is detected.

3 Claims, 6 Drawing Figures

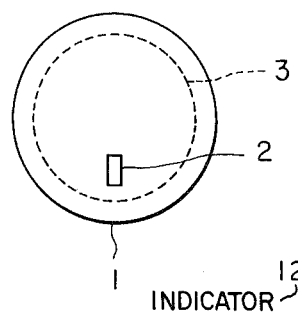
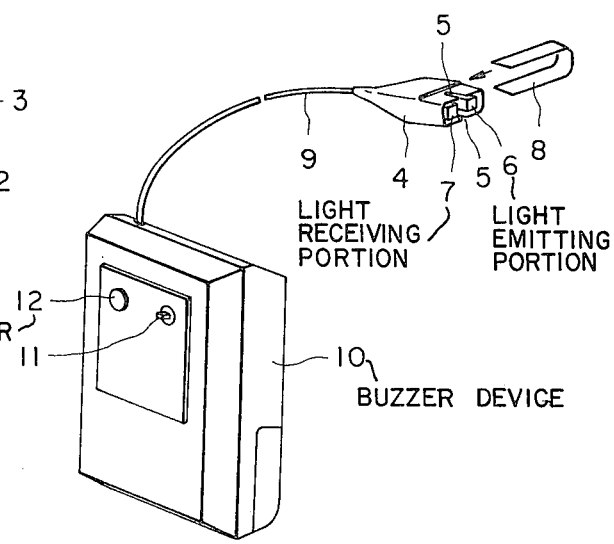
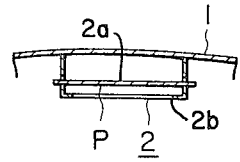
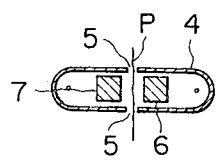
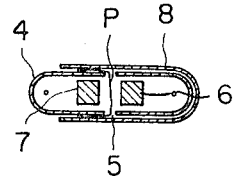
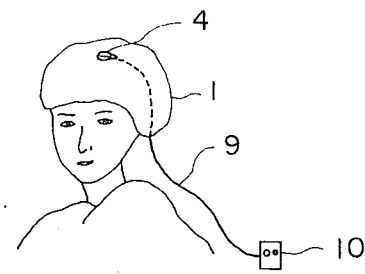

DETECTING METHOD AND APPARATUS FOR PERMANENT WAVE HAIRDRESSING

BACKGROUND OF THE INVENTION

The present invention relates to a detecting method and an apparatus for detecting a condition of waves in permanent wave hairdressing.

Permanent wave hair is produced with hair curled on a number of rods using tools and chemical liquid for waving in a cold manner or otherwise in a hot manner. The condition of waves must be ensured by locally rewinding the curl after a constant lapse of time, by feeling with ones fingers, and by observation in either the cold or hot prior art manner. Thus such an experimental technique requires that a sixth sense be used. However, such conventional method are disadvantageous in that the hair is insufficiently permed or damaged due to errors in timing adjustment since the wave set requires a constant lapse of time. These methods are ineffective and it is troublesome to inspect the wave condition everytime, in particular, in a crowded beauty saloon.

More specifically, there are many differences of the conditions of the permanent waves due to individual differences of hair properties, and even in one person there are delicate differences in the time period required for suitable permanent waves due to factors such as hair temperature, hair condition and health, a temperature difference in seasons, a kind of chemical liquid for waves and the like.

For this reason, the beautician must hairdress always in the optimum condition preparing cards in which individual hair properties, a required time for the wave set, and the like are recorded.

SUMMARY OF THE INVENTION

In order to overcome the above noted defects, an object of the present invention is to provide a simple and effective detecting method and an apparatus therefor for mechanically and chemically detecting the condition of permanent waves which are under the optimum condition.

Another object of the present invention is to provide a novel method and an apparatus therefor to solve troubles concerning the required time for the completion of the permanent wave, which has been considered intricate.

Also, according to the present invention, technical difficulties inherent to the prior art such as a damage generated due to the excessive lapse of time for the permanent wave and a poor hairdressing due to insufficient time thereof are completely eliminated.

These and other objects of the present invention will be apparent by the following description and the accompanying drawings.

BRIEF DESCRIPTION OF THE DRAWINGS

A spirit and scope of the present invention will be apparent from the appended claims. The present invention will be hereinafter described on the basis of the specific embodiments shown in the accompanying drawings; in which FIG. 1 is a plan view of a head cap, showing an embodiment of a detecting method according to the present invention;

FIG. 2 is an enlarged cross-sectional view of the attachment portion of a lead acetate test paper P hereinafter simply referred to as the "test paper P";

FIG. 3 is a perspective view of a detecting apparatus according to the present invention;

FIG. 4 is a cross-sectional view of a signal generating device used in the present apparatus;

FIG. 5 is a similar cross-sectional view of the signal generating device to which the test paper P is attached by a clip member; and FIG. 6 is an embodiment in which the detecting apparatus is used for a person.

DETAILED DESCRIPTION OF THE INVENTION

The present invention is applicable to the prior art manner of using a desired amount of a wave chemical liquid during the hairdressing, the winding operation of hair, the addition of heat under a constant temperature by a heater in case of the hot type permanent wave, and the like, all of which are used in a modern beauty salon. For the adjustment of a constant period of time for hairdressing, in the inner peripheral surface of a transparent head cap 1 is formed a support 2 to which a strip-shaped lead acetate test paper P is attached to as to be adapted to be in contact with hair provided with wave chemical liquid when put on a person's head. It is obvious that any attachment manner of the test paper to the interior of the head cap 1 may be used. In FIGS. 1 and 2, a box member 2a made of suitable elastic or rigid material extends downward from the under surface of the head cap 1. The box member 2a has a hole 2b through which gas generated in the cap is introduced, and the test paper P is secured suitably in the box 2a. Reference numeral 3 denotes a rubber ring for sealing an inner portion of the cap. The support portion 2 is so constructed so as to contact surfaces of the test paper P bridged and supported in the inner portion of the cap with the gas generated in the cap to thereby prevent the leakage of the generated gas therefrom. With such a construction, in the cold type, it may be used without any additional job and in case of the hot type, it is heated at constant temperature by using a heater (not shown). As time lapses, due to the body temperature or rapidly due to the heater, a sulfur component containing thioglycolic acid, which is a main component of the wave chemical liquid to be used, is converted into a minute amount of hydrogen sulfide gas and evaporates out of the hair. The hydrogen sulfide gas chemically reacts with the test paper P causes it to change from a brown color to a black color. According to repeated experiments, it has been found that when the density throughout the test paper P is changed into a dark black color the wave is best formed. Therefore, the desired wave set is achieved in a well known manner as indicated by the chemical maker, in view of subjective conditions such as personal difference in the hair property, the environmental condition such as a season and a room temperature, and objective conditions such as a chemical liquid amount and a heating temperature. Attention is not drawn to the lapse of time and the optimum condition of the permanent waves is automatically indicated when the test paper changes to a black color, to thereby provide an effective and reliable detector.

Accordingly, in the present invention, it is not necessary for the beautician to remove the rod clips on which the hair is wound after a necessary lapse of time in the wave set as in the prior art, and it is only necessary to confirm the optimum wave condition due to the color of the test paper. As previously indicated, it changes to a dark color which may be observed from the outside of the cap, eliminating additional operations. This will provide an effective method improving the prior art manner which has required intricate hairdressing operations.

A detecting apparatus for embodying the above-described method will be hereinafter described. The detecting device generally consists of a signal generator and a buzzer. In FIG. 3, it is composed of the signal generator 4, a slot 5 formed in a receiving portion, a light emitting portion 6 of a light emitting diode, a light receiving portion 7, an elastic clip 8, a lead wire 9, a buzzer device 10 encasing an electric power supply, a buzzer and the like, a switch 11, an indicator 12 and a cap 13. Thus the apparatus comprises the signal generating means 4 and the buzzer means 10, the test paper P is held at the slot 5 and fastened to the signal generating means with the clip 8 so that the test paper P is in contact with the hair within the cap 1 as shown in FIG. 6. When the test paper P is changed into a dark color having a predetermined density, the signal generating circuitry for the light emitting diode is interrupted. Then, the buzzer means is operated in response to the interruption to generate warning sounds. Completion of the permanent wave is detected and indicated. Accordingly, the condition of the wave is automatically announced with ease without observation thereof.

Of course, the above-described apparatus is applicable to either cold type and hot type, and there is only a difference between both types in the lapse of time required for the change in color of the test paper P.

The prior art technique depending on the beautician's experience and sixth sense with respect to the required time for the permanent wave is greatly improved or enhanced by the above proposed method and apparatus enabling the combined chemical and mechanical detection, thereby eliminating the additional jobs. In particular, according to the present invention, troubles of the required time for the completion of the wave, which has been heretofore considered intricate are solved.

Also, according to the present invention, technical difficulties inherent to the prior art such as a damage generated due to the excessive lapse of time for the permanent wave and a poor hairdressing due to insufficient time thereof are completely eliminated.

What is claimed is:

1. An apparatus for detecting a condition of permanent waves in hair during a permanent wave hairdressing procedure which produces hydrogen sulfide gas, comprising:
    signal generating means;
    a lead acetate test paper connected to said signal generating means, said lead acetate paper changing color when exposed to said hydrogen sulfide gas;
    a sealable head cap having an attachment portion on an under surface, said lead acetate test paper being attached to said attachment portion formed on said under surface of said cap; and
    buzzer means connected to said signal generating means, said buzzer means generating warning sounds when activated by said signal generating means when said lead acetate test paper is changed into a dark color of a predetermined constant density.

2. The apparatus claimed in claim 1, wherein said signal generating means comprises a light generating portion and a light receiving portion disposed on opposite sides of a slot which receives said lead acetate test paper.

3. The apparatus claimed in claim 2, further comprising a clip for holding said lead acetate paper in said slot.

* * * * *